United States Patent [19]

Adelson

[11] Patent Number: 5,054,930
[45] Date of Patent: Oct. 8, 1991

[54] SCANNING APPARATUS

[75] Inventor: Alexander Adelson, Peekskill, N.Y.

[73] Assignee: Intec, Corp., Trumbull, Conn.

[21] Appl. No.: 487,572

[22] Filed: Mar. 2, 1990

[51] Int. Cl.$^5$ .............................................. G01N 21/89
[52] U.S. Cl. ...................................... 356/429; 350/6.8
[58] Field of Search ................ 356/429, 431; 250/563, 250/571, 572; 350/6.6, 6.8

[56] References Cited

U.S. PATENT DOCUMENTS

| | | | |
|---|---|---|---|
| 3,293,655 | 12/1966 | McNaney | 350/6.8 |
| 4,160,913 | 7/1979 | Brenholdt | 356/431 |
| 4,277,178 | 7/1981 | Cushing et al. | 356/431 |
| 4,460,273 | 7/1984 | Koizumi et al. | 250/563 |

Primary Examiner—Richard A. Rosenberger
Attorney, Agent, or Firm—Sprung Horn Kramer & Woods

[57] ABSTRACT

A high speed scanning system for scanning a moving target. Comprising rotating a polygonal mirror with a plurality of mirrored sides about an axis of rotation at the center thereof directing a first laser beam at the polygonal mirror along a first path intersecting one mirror face at a time and reflecting at a given useful angle to scan a target moving in at least one direction with a first scan by each mirror face in one scan direction, wherein an imaginary line extending the first path beyond the intersected mirror face is offset from the axis of rotation. A second laser beam is directed at the polygonal mirror along a second path intersecting the same one mirror face at a time as the first beam and reflecting at said given useful angle to scan and the moving target with a second scan in the one scan direction delayed in time from the first scan by each mirror face, wherein an imaginary line extending the second path beyond the intersected mirror face is offset from the axis of rotation and wherein the second path forms an angle with respect to the first path which is greater than said given useful angle, whereby two scans are effected for each mirror face. The laser beam light directed at the moving target is then detected.

40 Claims, 4 Drawing Sheets

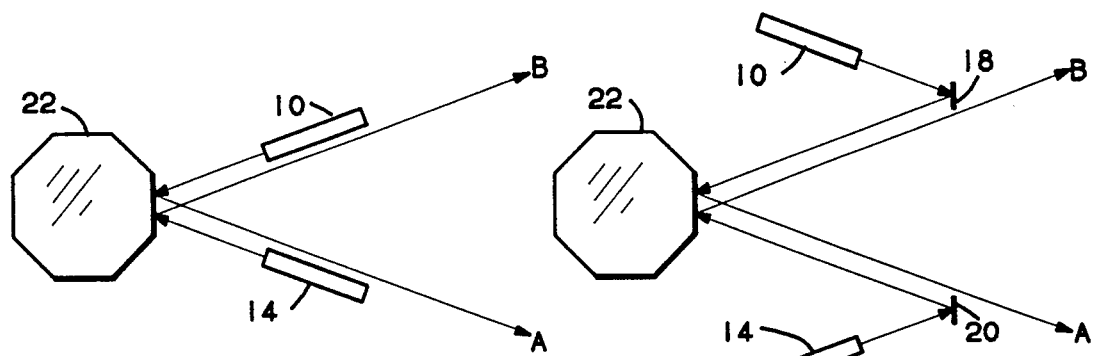
FIG. 5a
FIG. 5b
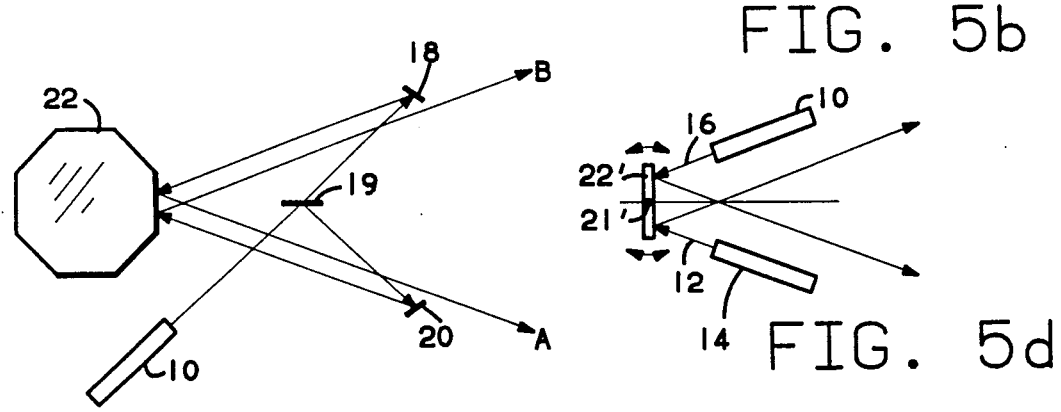
FIG. 5c
FIG. 5d
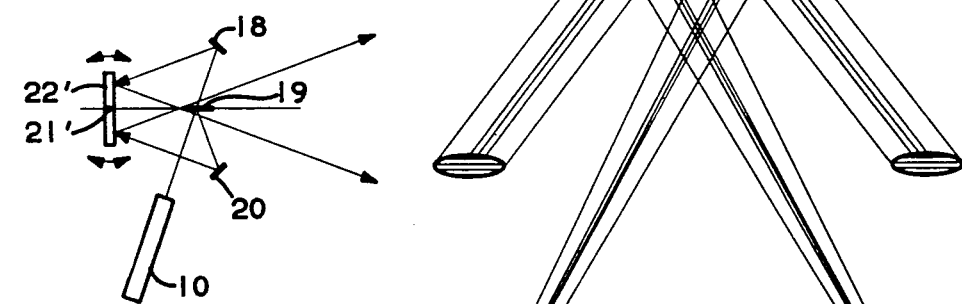
FIG. 5e
FIG. 6
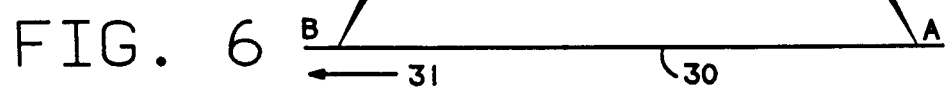

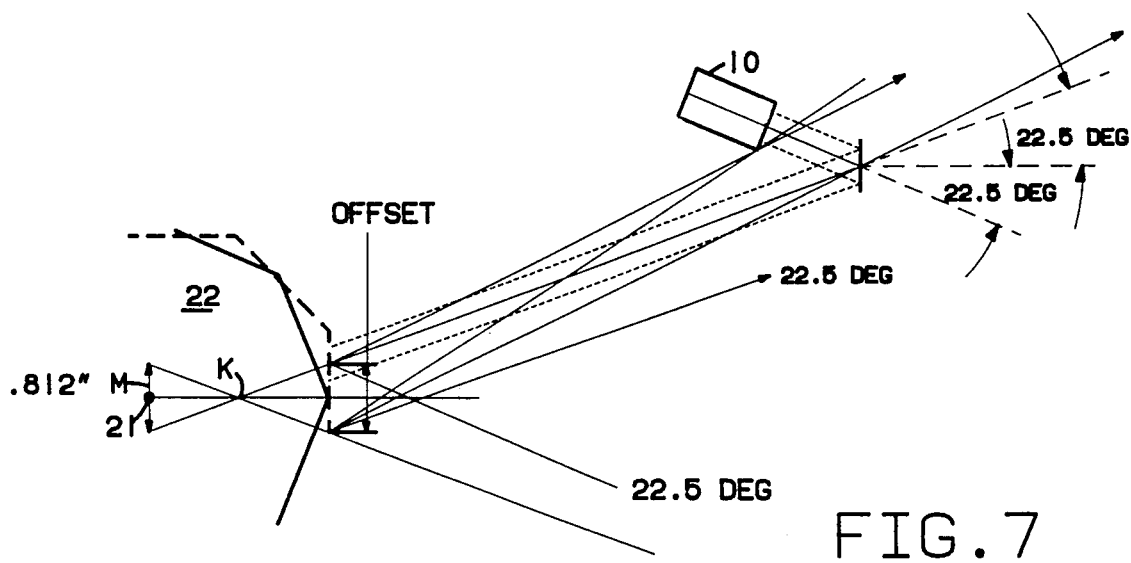
FIG. 7
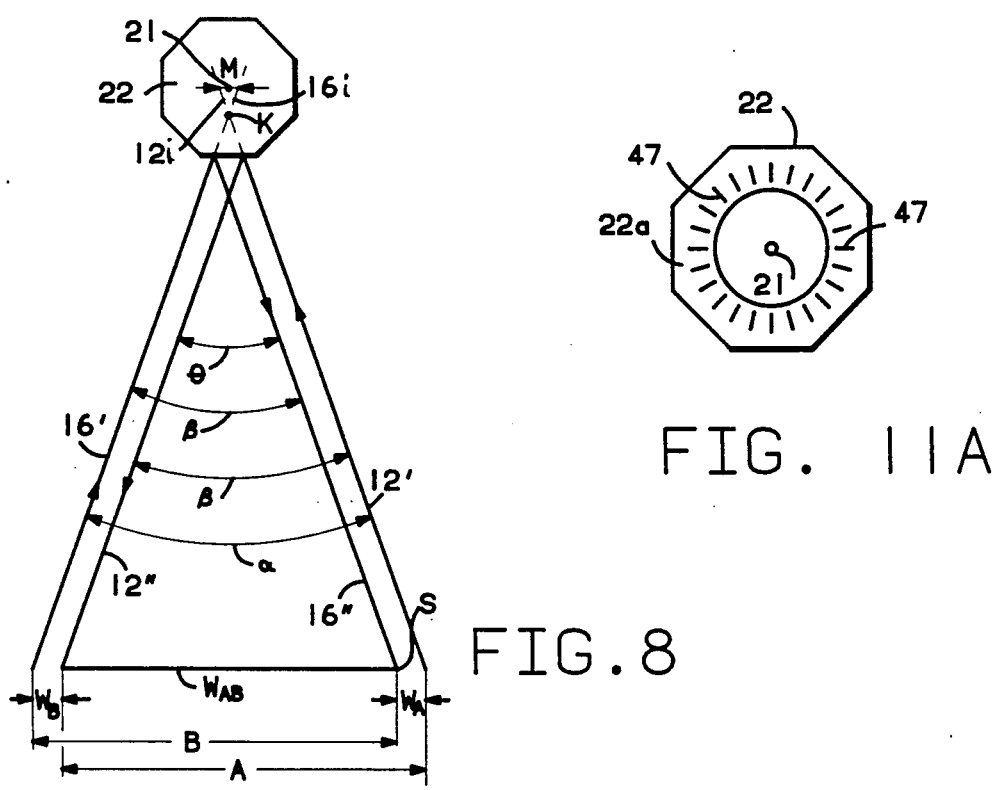
FIG. 8
FIG. 11A
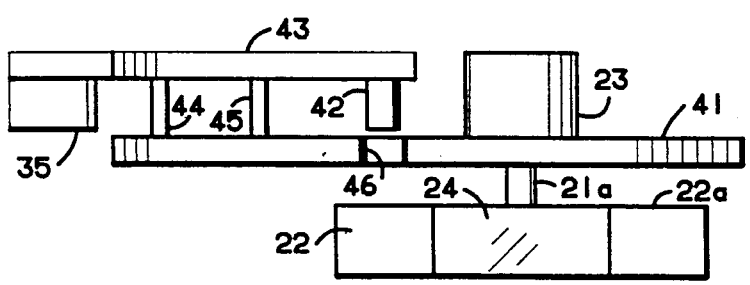
FIG. 11B

SCANNING APPARATUS

BACKGROUND OF THE INVENTION

The present invention is directed to a scanning apparatus and in particular to a high-speed scanning apparatus for detecting objects or events on a moving target such as a web for the purpose of detecting changes or faults therein.

Scanning apparatus are known in the prior art, for example as disclosed in U.S. Pat. No. 4,265,545. The disadvantage of that and other prior art systems, is that in order to accommodate wide moving webs having widths of up to 60" and traveling at speeds of up to 1200 feet per minute, scanners, and in particular inspection systems, need complex and costly optical elements in order to detect flaws at a sufficient level of resolution.

SUMMARY OF THE INVENTION

The main object of the present invention is to overcome the disadvantages of the prior art scanning systems and to provide a scanning system which is low cost, yet capable of accommodating dynamic or non-constant web speeds of up to at least 1200 feet per minute and web widths of up to 60" and more and detecting flaw widths 0.004" and smaller.

Another object of the present invention is to provide a two optical axis path geometry which enables a multi-sided polygon mirror or a single sided mirror to act as if it has twice the number of sides in order to decrease the cost of the mirror while increasing the efficiency thereof.

Still another object of the present invention is to provide an optical path offset to enable a minimum polygon mirror width in order to decrease the cost of the polygon mirror.

A further object of the present invention is to provide optical path declination in order to enable a minimum size of the system with the fewest parts.

A still further object of the present invention is to provide optical path declination to enable an optimum two axis geometry without limiting the maximum useful scan line of the scanning apparatus.

A further object of the present invention is to provide a scan spot geometry that allows for high web speed at relative low polygon rotation speed, but still retains high resolution flaw or event detection capability.

Another object of the present invention is to provide a series of ratios and constants associated with the system optical elements in order to define a pragmatic solution set to enable low cost with high resolution.

Still another object of the present invention is to provide a scanning apparatus with a moving scanning mirror and a laser light source having a novel ratio of spot size length and width.

A further object of the present invention is to provide control of the laser beams to effect a maximum useful scan angle while preventing interference.

Another object of the present invention is to provide a spatial clock for controlling the scan field position on a web.

These and other features and advantages of the present invention are achieved in accordance with the present invention by a scanning apparatus, preferably one operating at high speed and preferably for scanning a moving target and comprising a mirror which preferably is a polygon with a plurality of sides and a center having an axis of rotation at the center thereof and a mirror face at each side thereof. The mirror rotates about the axis of rotation and means are provided for forming a first laser beam for directing same at the polygonal mirror along a first path which intersects one mirror face at a time during rotation for reflection at a given useful angle to effect a first scan by each mirror face in one scan direction of a target moving in at least one direction. The first path extends on an imaginary line beyond the intersected mirror face and is offset from the axis of rotation. Means are also provided for forming a second laser beam and for directing the second laser beam at the mirror along a second path which intersects the same mirror face being intersected by the first laser beam for reflection at the given useful angle to effect the second scan in the one scan direction of the moving target which is delayed in time from the first scan for that mirror face. An imaginary line extending the second path beyond the intersected mirror face is offset from the axis of rotation and wherein the second path forms an exit angle with respect to the first path which is greater than the given useful angle. As a result of this structure, two scans are effected for each mirror face. The laser beams directed at the moving target are detected and a signal is produced corresponding thereto.

In one preferred embodiment, the means for forming the first and second laser beams each comprise a high energy source of light such as a laser light generator which is a laser tube or preferably a semiconductor laser diode. In an alternative embodiment, the means forming the first and second laser beams comprises a single laser light source and a mirror for splitting the laser beam emitted from the laser light source. The first and second laser beams are preferably directed at the target by reflecting mirrors.

The first and second paths of the laser beams preferably have a non-zero acute angle of declination with respect to a plane perpendicular to the axis of rotation.

Moreover, in accordance with the present invention, the means forming the first and second laser beam comprise means defining a spot size having a given width in the scan direction and a given length in the direction of movement of the target and wherein the ratio of the length to the width is from 11–22:1, preferably from 14–19:1 and most preferably 16.6:1. The spot width is preferably less than or equal to 0.011".

In another preferred embodiment of the present invention, the means for rotating the mirror effects a spot overlap of at least 5% between successive first and second scans.

In accordance with the present invention, the polygon has a plurality of sides, preferably eight sides and the angle between the first and second beams is approximately $360° \div N$, where N is equal to the number of sides of the mirror.

In an alternative embodiment of the present invention, the mirror has one face and a pivot at the center thereof and the mirror oscillates about the pivot axis and the first and second beams are directed on the one face of the mirror and wherein the paths of the beams are offset from the pivot axis at the center of the mirror and the angle formed between the beams is greater than the useful angle as in the case of a polygon.

In a still further preferred embodiment of the present invention, the first and second laser beams are controlled so that one beam is off the web while the other beam is scanning the target. This control is carried out by preferably positioning two photodetectors upstream of the target scan line which is scanned by the laser beams and which generate a prescan signal which informs the system which beam is scanning and therefore to produce a start of scan signal after a predetermined delay which turns off the other laser beam and produce a scan field signal after a predetermined delay, which defines a scan window during which time the laser beam is in a scan path which covers a desired scan width of the web.

In another preferred embodiment, the scan signals are controlled by a spatial clock generated by the rotation of the mirror.

These and other features of the present invention will be described in more detail in the following detailed description of the invention taken with the attached drawings, wherein:

BRIEF DESCRIPTION OF THE DRAWINGS

FIGS. 5 a-e show alternative embodiments of the present invention;

FIG. 6 shows the scan ray traces of the two laser beams and their location on the mirror face;

FIG. 7 is a detailed view of the scanner ray trace and location;

FIG. 8 shows the angular offset of the laser beams in accordance with the present invention;

FIGS. 11A and 11B are schematic views of another embodiment according to the present invention.

DETAILED DESCRIPTION OF THE INVENTION

Figure 1:
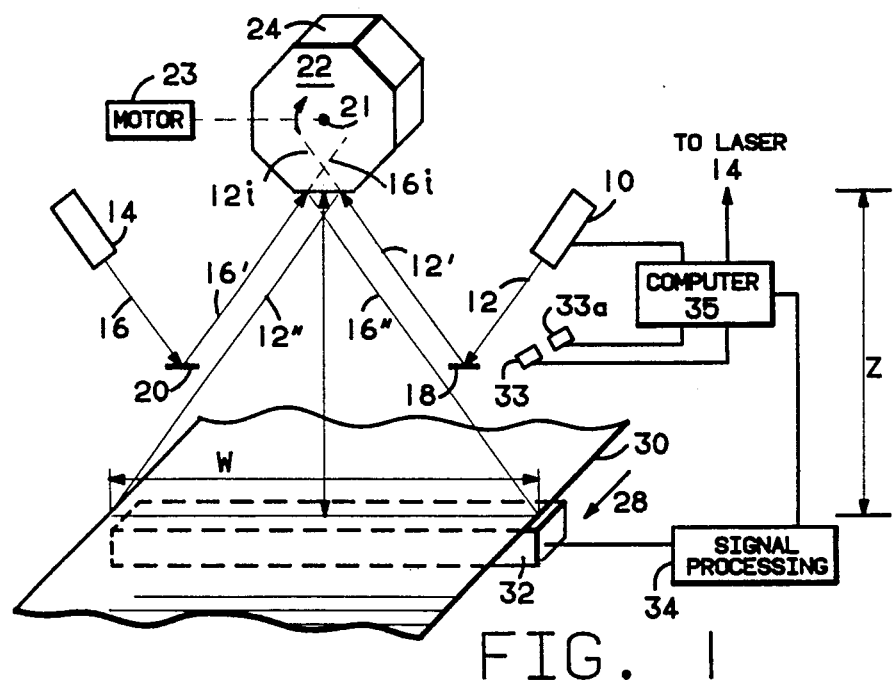
FIG. 1 is a perspective view of a scanning apparatus according to the present invention.

In the following description, like elements bear the same reference numerals.

Referring now to FIG. 1, the scanning apparatus in accordance with the present invention is capable of operating with material 30 having a width W of up to 60" and greater which moves in a direction 28 with a speed of up to 1200 feet per minute and greater. It should be of course recognized that the apparatus in accordance with the present invention will scan a stationary target and that the apparatus in accordance with the present invention could be used for scanning material for flaw detection, for optical character recognition, symbol reading, etc.

The minimum resolution, which is preferably the size of a defect to be detected, is on the order of 0.004" or less wide for a scan of up to 60" or greater. This scanner is also capable of scanning all portions of the web 30 as it is moving along direction 28.

As shown in FIG. 1, two laser sources 10, 14 are provided for producing laser beams 12 and 16. The laser sources can be any conventional laser light sources such as a gas tube laser, particularly a helium neon laser, however the preferred embodiment of the present invention is that lasers 10 and 14 be laser diodes producing laser beams having a wavelength of from 400 to 820 Nm, such as GaAlAs laser diode devices.

The laser beams 12, 16 are reflected as beams 12', 16' by folding mirrors 18 and 20 to the faces of a rotating polygon mirror 22 which rotates about an axis of rotation 21 and is driven by motor 23. The polygon mirror 22 is shown having eight faces 24, however it should be clear that more or less faces can be used within the spirit of the invention.

The beams 12' and 16' are directed by mirrors 18 and 20 so that the beams intersect one face 24 at a time and are reflected as beams 12", 16". When imaginary lines 12i and 16i are drawn to extend beams 12' and 16' respectively beyond the intersected face, these imaginary lines 12i, 16i are offset from axis of rotation 21. The two imaginary lines 12i 16i intersect at a point spaced from the axis of rotation 21 by a predetermined distance as will be discussed hereinafter.

Figure 2:
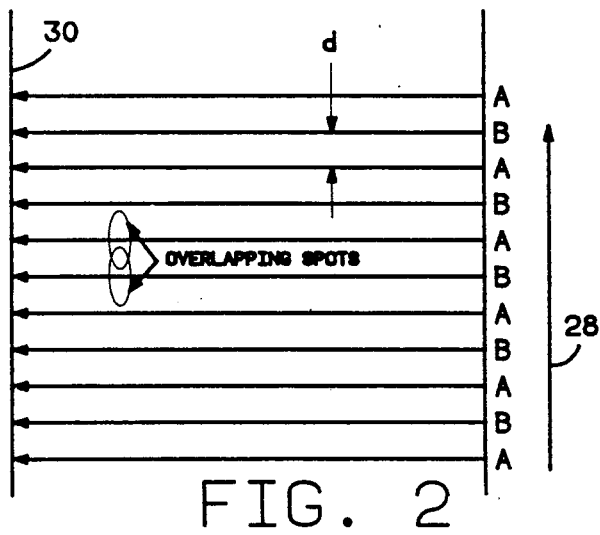
FIG. 2 is a top view of scan lines on a moving web obtained in accordance with the apparatus shown in FIG. 1.

As a result of the use of two beams with the aforementioned offset, as shown in FIG. 2 for each face of the polygon 22, the scanner in accordance with the present invention produces two scan lines A and B scanning across web 30 in the same direction as shown with the arrows and delayed in time with respect to each other. Thus polygon 22 effects 16 scans per rotation, as if the polygon had 16 sides instead of 8. The ability to generate two scans per face of a polygonal mirror realizes a substantial savings in system costs, since the cost of a polygonal mirror is directly related to the number of faces thereon. Moreover, the system in accordance with the present invention makes use of a minimum amount of area on each face, enabling the polygonal mirror to be smaller and thus more economical since the smaller polygon allows a smaller motor which allows for a smaller package and thus a smaller device.

Figure 3:
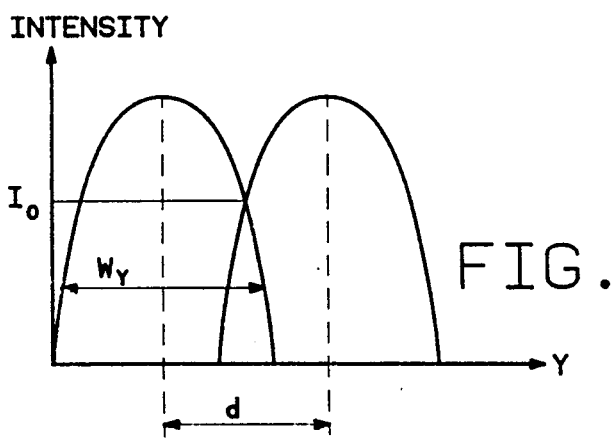
FIG. 3 is a graph of the intensity of overlapping spots of the scan lines of FIG. 2.

Web inspection requires observation or scanning of all of the web area. Therefore, to carry this out in accordance with the present invention, motor 23 rotates the mirror 22 so that the two scan lines A, B shown in FIG. 2 are sufficiently close to each other that the scan spots formed by each beam will overlap in the direction of movement 28 of web 30. The overlap of the spots is preferably at least 5% of the area thereof and most preferably 10 to 20%. As is shown in FIG. 3, which shows the intensity level of the spot with respect to the direction of movement 28, the overlapping of the spots achieves a more even intensity distribution of the energy applied to receiver 32 for conversion to an electrical signal which is thereafter processed in signal processor 34. The receiver 32 and signal processor 34 are of the type disclosed in copending U.S. application Ser. No. 07/487,571 filed on the same day as this application and by the same applicants and assigned to the same assignee, the disclosure of which is incorporated herein by reference. The level of intensity I where the two spots overlap and the spot size in the direction of movement $W_y$ determine the ability of the detector or receiver 32 to detect small signals and the amount of noise that the system can tolerate. Thus in order to resolve defects as small as 0.004" wide and less, the spot size in accordance with the present invention is less than or equal to 0.011" and the ratio of the length of each spot to its width $W_y$ is from 11-22:1.

The size of the polygon mirror 22 for the scanner in accordance with the present invention is determined by the width of the facet or mirror face 24 and the number of faces required. The width of the face 24 is determined by the size of the spot forming laser beam thereon. In order to determine these parameters, it is necessary to determine the useful angle needed to scan a web which has a width of up to 60″ or greater. This useful angle $\theta$ is then used to determine the number of faces on the polygon and the length of each face in accordance with the following equation:

$$\theta = (720° \div N)(1 - D/L)$$

where N=the number of faces on the polygon, L=the length of the face and D=the laser beam size on the face.

Figure 4:
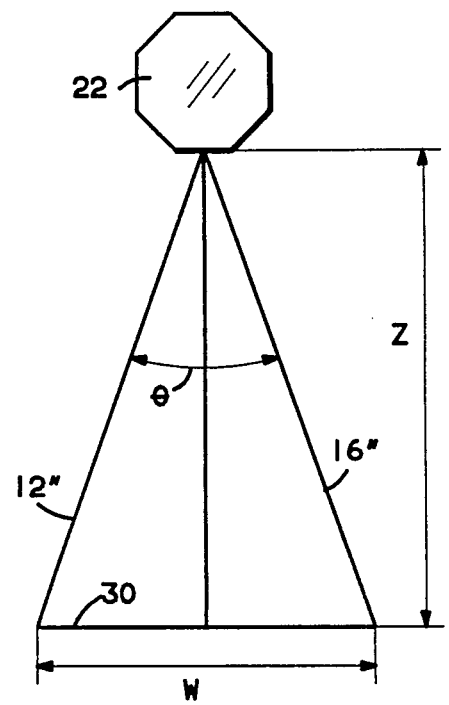
FIG. 4 shows the useful angle of the scanner.

The useful angle $\theta$ is determined by the angle subtended by the web 30 from the polygon mirror 22 as shown in FIG. 4. Thus if the width W of the web 30 is a constant value in a range of from 40-60″, the angle $\theta$ is determined by the distance Z of the face of the polygon 22 from the web 30. However, a fundamental limitation in such a system is the tangential effect of the scan line curvature which limits the useful depth of focus. Since all focused optical systems have an inherent depth of focus, unless a web is curved so as to match the radius of curvature of the scan path (which it is not because the web is flat), depth of focus is a significant factor. Thus if one requires that the spot width not exceed 0.0085″ at any point on the web, which is easy to do if the angle $\theta$ is small, this brings about a increase in spot speed which requires an increase in frequency response of the receiver and in turn brings about a higher level of noise which reduces the ability of the system to resolve objects of smaller sizes. In a preferred embodiment of the present invention, the distance Z is preferably 70-80″ and most preferably 75″ which yields a useful angle of 37°. From the formula set forth hereinabove, if one were to use a 16 sided polygon, the equation yields a polygon face having a length of 1.45″ and a diameter of 7.4″. However, because of the features of the present invention, the same size face can be utilized on an eight sides polygon and thus the diameter of the polygon is significantly reduced.

FIGS. 5 a-e show alternative embodiments wherein two scanning lines A and B are obtained from each face of a moving mirror 22. In FIG. 5a, laser modules 10 and 14 direct their beams on a straight path directly to each face of polygon 22. In the embodiment of FIG. 5b, which is similar to that shown in FIG. 1, laser modules 10 and 14 direct the outputs thereof to folding mirrors 18 and 20 respectively in order to thereafter direct their beams onto each face of polygon 22. In the embodiment shown in FIG. 5c, a single laser module 10 is utilized and a beam splitter 19 is placed directly in the path thereof to split the output of laser module 10 into two beams which are directed onto folding mirrors 18 and 20 and thereafter onto each face of polygon 22.

FIGS. 5d and 5e show alternative embodiments of the invention wherein, instead of a rotating polygon, a single sided mirror 22′ is used as the scanning element and the mirror 22′ is oscillated about its center 21′ to effect scanning. In the embodiment of FIG. 5d, laser sources 10 and 14 are aimed directly at the face of mirror 22′ in such a way that the direct beams 12 and 16 are offset from the center 21′. In the embodiment of FIG. 5e, a single laser 10 is utilized with the beam splitting mirror 19 and folding mirrors 18 and 20 which direct the beams to the face of mirror 22 so that they are offset from the center 21′.

As a result of the structure shown in FIGS. 5d and 5e, the mirror 22′ generates two scan lines A,B for each oscillation thereof so as to appear as if it is a mirror with two faces. The only difference between those embodiments and that of FIGS. 5 a-c, is that scan lines A and B are in opposite directions on the web.

FIG. 6 shows the bundle of rays forming the two laser scans A and B and how beams are aimed at adjacent areas 24A and 24B of the same polygon face 24. Referring also to FIG. 8, the included angle $\alpha$ between the beams 12′, 16′ is greater than the useful angle $\theta$ and, in order to avoid mechanical interference, is greater than the reflecting angle $\beta$ of each beam.

FIG. 7 shows the timing of the two scans resulting from the rotation of the polygon 22. The continued rotation of the polygon brings the first beam 12″ to the center of the scan line A while the other beam 16′ moves to the next face of the polygon. When the first beam 12″ completes the scan line A, the second beam 16′ is now in position on the adjacent mirror face and ready to start the next scan line B. This is repeated continuously as the polygon rotates.

As a result of the two beam approach, the system is asymmetrical with respect to the two scans. In order to achieve a maximum useful scan length, beam 12′ is displaced from 16′ by a constant value. This displacement results from the beams 12′ and 16′ crossing at their imaginary extensions 12i, 16i at point K and extending thereafter such that the distance between the two beams at the axis of rotation 21 is a distance M which in the preferred embodiment of the present invention is 0.812″. As a result of this displacement, the central rays of laser beam 12′ and laser beam 16′ are displaced. The width of the laser beam 12′ projected on the polygon face during entry (the solid polygon line) and exit (the dashed polygon line) can be seen in FIG. 7. This makes a maximum use of the area of the face and reduces the size of the polygon to a practical minimum.

It should also be clear from FIG. 8 that as a result of this arrangement, there is a portion of the scan for lines A and B which is lost. This portion on both sides of the common line $W_{AB}$ cannot be used since the portion $W_A$ is scanned by line A but not by line B and the portion $W_B$ is scanned by line B and not by line A. As a result, the use of scan areas $W_A$ and $W_B$ would result in a failure to scan certain portions of the overall web and thus would be undesirable. Therefore only the common area $W_{AB}$ which is utilized for scanning and this area $W_{AB}$ is made equal to the web width W or if desired, a portion of the web width. This is true when the edges of the web are salvage that is to be removed or discarded.

Figure 9:
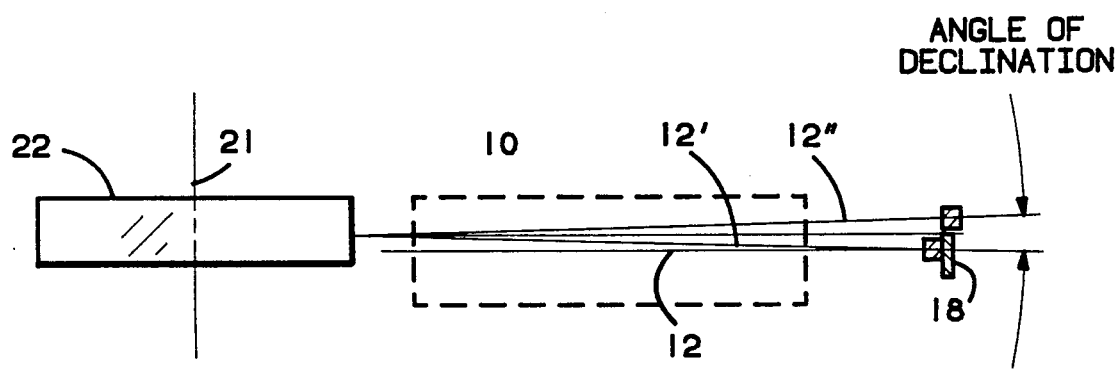
FIG. 9 shows a scanner ray trace and location of the angle of declination according to the present invention.

Referring to FIG. 9, in order to make the system more compact, in the embodiment wherein the folding mirrors are used as is shown in FIG. 5b and in FIG. 1, an angle of declination is utilized for the beam 12 going from the laser 10 to folding mirror 18, an angle of declination for the beam 12′ going from folding mirror 18 to polygon 22 and an angle of declination of the beam 12″ going from the polygon 22 to the web 30. As a result of these angles of declination, the laser, folding mirror and polygon do not lie in the same plane. This results in the beam 12″ and 16″ being displaced in such a way that it can pass over the folding mirror on its way to the web.

In accordance with the invention, in order to prevent interference by the beams and maximize the useful scan area $W_{AB}$ as shown in FIG. 8, the scan lines A and B are controlled so that when one of the beams is in the scanning field $W_{AB}$ the other beam is outside of field $W_{AB}$ and is thereafter turned off. Moreover, the system must be able to accurately generate a scan field signal corresponding to a desired scan width on the web.

Figure 10:
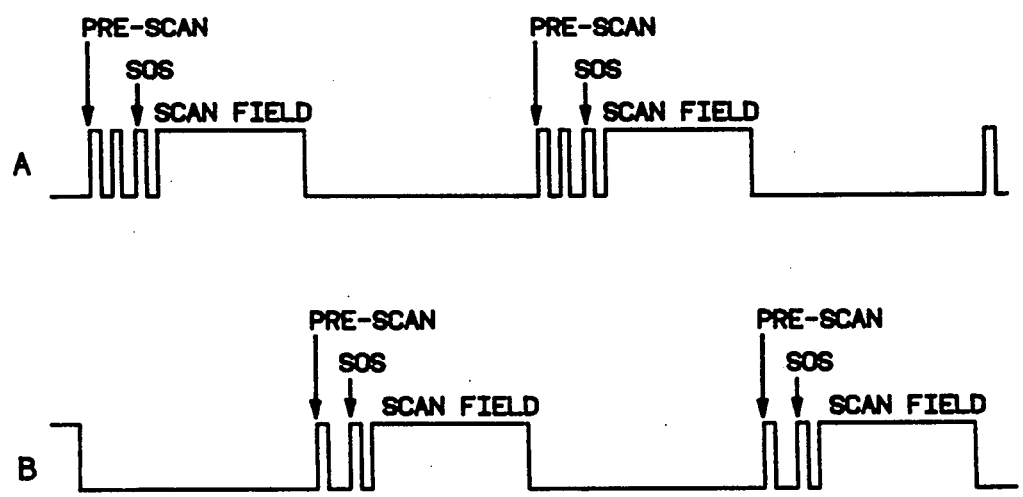
FIG. 10 shows a waveform diagram of the signals used to control the laser light sources in accordance with the present invention.

In order to carry this out, a fixed reference tracking system is used wherein two photodetectors 33, 34 (FIG. 1) are disposed in the scan beam paths shown in FIG. 8. Photodetector 33 is positioned to be in the scanning field $W_{AB}$, preferably at the point S in FIG. 8 which is at the earliest point thereof and which is scanned by both of the beams. Photodetector 33 is disposed in the area $W_A$, that is, in the beam path of beam A but not beam B. Thus, as shown in FIG. 10, beam A produces two pre-scan signals from the two photodetectors 33, 33a while beam B produces a single pre-scan signal from photodetector 33. These pre-scan signals are sent to computer 35 which, by means of simple combinatorial logic can determine from the one or two pre-scan signals whether the system is using scan B or scan A. Because of the unsymmetry of the two beams, there is a difference in the delay between the starting of the scan field after the pre-scan signals generated by the two beams. Thus the computer 35 can calculate the desired delay depending on which of the beams is in use and generate a start of scan signal based on that calculated delay and the use of an internal clock. At the time of the start of scan signal (SOS), the other beam, which is now outside the scan field, is shut off so that there will be no interfering signals generating incorrect data. This is carried out by the computer which is connected to the two lasers 10 and 14. After another predetermined delay based upon the computer's clock, the scan field signal is produced which permits the receiver 32 to receive and evaluate energy from the web. FIG. 10 shows the relative timing of the signals for scans A and B.

In another embodiment using edge tracking, only photodetector 33 is used to produce the pre-scan signal. The SOS signal is produced after a predetermined delay. The scan field signal is produced when the scanner senses the edge of the web at point S. Then the clock starts to run to control the length of the scan field.

The internal clock of the computer is independent of the rotation of the mirror 21. In another embodiment of the invention as shown in FIGS. 11A and 11B, a clock is used which is synchronous with the rotation of the mirror 21 and thus capable of compensating for changes in the speed of rotation that might occur. As shown in FIG. 11A, the mirror 21 has time marks 47 disposed around the axis of rotation 21 on the rear face 22a.

The mirror 21 is mounted, as shown in FIG. 11B, on a board 41 with motor 23 having a shaft 21a which rotates about axis of rotation 21. Board 41 has a hole 46 and a photodetector 42 disposed therebehind on another board 43 mounted on board 41 by connectors 44, 45. Computer 35 is also mounted on board 43 and is connected to photodetector 42 to receive pulse signals therefrom corresponding to the time marks as the motor rotates the mirror 21. This system forms a spatial clock for the computer so that the computer may base the predetermined delays on the number of clock pulses independent of variations in the rotational speed of the mirror.

In a particularly preferable commercial embodiment of the present invention, the offset ratio of the optical axis with respect to the polygon center of rotation is preferably 2:1. The offset is directly proportional to the beam width at the polygon face and the offset equals one half the beam width plus a small allowance for error. When two laser sources are used the offset distance K is two times the offset ratio. In the preferred embodiment, the width of the polygon mirror is 1.33 to 1.66" and is an eight sided polygon. The polygon mirror width to spot geometry ratio is 173:1 to 213:1. The polygon to web focal distance for maximum detection is 70–80". The spot geometry to resolution ratio is 11:1 to 22:1. The spot height to maximum web speed ratio is preferably 9300:1 minimum. Angle $\beta$ is $22\frac{1}{2}°\pm\frac{1}{2}°$ and the exit beam declination angle with respect to the entrance beam is $1.3°+2°-\frac{1}{8}°$.

It will be appreciated that the instant specification and claims are set forth by way of illustration and not limitation, and that various modifications and changes may be made without departing from the spirit and scope of the present invention.

What is claimed is:

1. A high speed scanning apparatus for scanning a moving target, comprising:

a polygonal mirror with a plurality of sides and a center and having an axis of rotation at the center thereof and a mirror face at each side thereof;

means for rotating the mirror about the axis of rotation;

means for forming a first laser beam and for directing the first laser beam at the polygonal mirror along a first path which intersects one mirror face at a time during rotation for reflection at a given angle to effect a first scan by each mirror face in one scan direction of a target moving in at least one direction, wherein a first imaginary line extending the first path beyond the intersected mirror face is offset from the axis of rotation on one side thereof;

means for forming a second laser beam and for directing the second laser beam at the polygonal mirror along a second path which intersects the same one mirror face at a time as the first beam for reflection at said given angle to effect a second scan in the one scan direction of the moving target delayed in time from the first scan by each mirror face, wherein a second imaginary line extending the second path beyond the intersected mirror face is offset from the axis of rotation on another side thereof and intersects the firs imaginary line behind the intersected mirror face and wherein the second path forms an angle with respect to the first path which is greater than said given angle, whereby two scans are effected for each mirror face; and means for detecting the laser beam light directed at the moving target.

2. The apparatus according to claim 1, wherein the means for forming the first and second laser beams each comprise a laser diode.

3. The apparatus according to claim 1, wherein the means for forming the first and second laser beams comprise a single laser diode and a mirror for splitting the laser beam from the laser diode.

4. The apparatus according to claims 2 or 3, wherein the means for directing the first and second laser beams comprises reflecting mirrors.

5. The apparatus according to claim 1, wherein the first and second paths have a non-zero acute angle of declination with respect to a plane perpendicular to the axis of rotation.

6. The apparatus according to claim 1, wherein the means for forming the first and second laser beams comprise means defining a spot size having a given width in the scan direction and a given length in the direction of movement of the target and wherein the ratio of the length to the width is from 11–22 to 1.

7. The apparatus according to claim 6, wherein the spot width is ≦0.011".

8. The apparatus according to claim 1, wherein the moving target comprises a web moving in a transport direction.

9. The apparatus according to claim 8, wherein the one scan direction is perpendicular to the transport direction.

10. The apparatus according to claim 1, wherein the polygon has 8 sides.

11. The apparatus according to claim 1, wherein the angle between the first and second beam paths is approximately 360°÷N, wherein N is equal to the number of sides of the mirror.

12. A high speed scanning apparatus for scanning a moving target, comprising:
 a mirror having one face and a pivot at the center thereof;
 means for oscillating mirror about the pivot axis;
 means for forming a first laser beam and for directing the first laser beam at the mirror along a first path which intersects the face for reflection at a given angle to effect a first scan of a moving target in one scan direction for each oscillation, wherein a first imaginary line extending the first path beyond the one face is offset from the pivot axis on one side thereof;
 means for forming a second laser beam and for directing the second laser beam at a mirror along a second path which intersects the mirror thereof for reflection at said given angle to effect a second scan of the moving target in a scan direction opposite said one scan direction and delayed in time from the first scan for each oscillation, wherein a second imaginary line extending the second path beyond the intersected mirror face is offset from the pivot axis on another side thereof and intersects the first imaginary line behind the intersected mirror face and wherein the second path forms an angle with respect to the first path which is greater than said given angle; whereby two scans are effected from the mirror face for each oscillation of the mirror; and
 means for detecting the laser beam light directed at the moving target.

13. The apparatus according to claim 12, wherein the means for forming the first and second laser beams each comprise a laser diode.

14. The apparatus according to claim 12, wherein the means for forming the first and second laser beams comprise a single laser diode and a mirror for splitting the laser beam from the laser diode.

15. The apparatus according to claims 13 or 14, wherein the means for directing the first and second laser beams comprises reflecting mirrors.

16. The apparatus according to claim 12, wherein the first and second paths have a non-zero acute angle of declination with respect to a plane perpendicular to the pivot axis.

17. The apparatus according to claim 12, wherein the means for forming the first and second laser beams comprise means defining a spot size having a given width in the scan direction and a given length in the direction of movement of the target and wherein the ratio of the length to the width is from 11–22 to 1.

18. The apparatus according to claim 17, wherein the spot width is ≦0.011".

19. The apparatus according to claim 12, wherein the moving target comprises a web moving in a transport direction.

20. The apparatus according to claim 19, wherein the scan directions are perpendicular to the transport direction.

21. A high speed scanning method for scanning a moving target, comprising the steps of:
 rotating a polygonal mirror with a plurality of mirrored sides about an axis of rotation at the center thereof;
 directing a first laser beam at the polygonal mirror along a first path intersecting one mirror face at a time and reflecting at a given angle to scan a target moving in at least one direction with a first scan by each mirror face in one scan direction, wherein a first imaginary line extending the first path beyond the intersected mirror face is offset from the axis of rotation on one side thereof;
 directing a second laser beam at the polygonal mirror along a second path intersecting the same one mirror face at a time as the first beam and reflecting at said given angle to scan and the moving target with a second scan in the one scan direction delayed in time from the first scan by each mirror face, wherein a second imaginary line extending the second path beyond the intersected mirror face is offset from the axis of rotation on another side thereof and intersects the first imaginary line behind the intersected mirror face and wherein the second path forms an angle with respect to the first path which is greater than said given angle, whereby two scans are effected for each mirror face; and
 detecting the laser beam light directed at the moving target.

22. The method according to claim 21, wherein the steps for directing the first and second laser beams each comprise forming the beams with a laser diode.

23. The method according to claim 21, wherein the step of directing the first and second laser beams comprises the steps of forming the first and second laser beams with a single laser diode and splitting the laser beam from the laser diode.

24. The method according to claims 22 or 23, wherein the steps directing the first and second laser beams comprises reflecting the beams with mirrors.

25. The method according to claim 21, wherein the step of directing the laser beams comprises forming the first and second paths with a non-zero acute angle of declination with respect to a plane perpendicular to the axis of rotation.

26. The method according to claim 21, wherein the step of directing the first and second laser beams comprises defining a spot size having a given width in the scan direction and a given length in the direction of movement of the target and wherein the ratio of the length to the width is from 11–22 to 1.

27. The method according to claim 26, wherein the spot width is ≦0.011".

28. The method according to claim 21, wherein the moving target is a web moving in a transport direction.

29. The method according to claim 28, wherein the one scan direction is perpendicular to the transport direction.

30. The method according to claim 21, wherein the polygon has 8 sides.

31. The method according to claim 21, wherein the angle between the first and second beam paths is approximately 360°÷N, wherein N is equal to the number of sides of the mirror.

32. A high speed scanning method for scanning a moving target, comprising:

oscillating a mirror having one face about a pivot axis at the center thereof;

directing a first laser beam at the mirror along a first path intersecting the face and reflecting at a given angle to scan a moving target in one scan direction with a first scan for each oscillation, wherein a first imaginary line extending the first path beyond the one face is offset from the pivot axis of rotation on one side thereof;

directing a second laser beam at the mirror along a second path intersecting the mirror face and reflecting at said given angle to scan and the moving target with a second scan in a scan direction opposite said one scan direction and delayed in time from the first scan for each oscillation, wherein a second imaginary line extending the second path beyond the intersected mirror face is offset from the pivot axis on another side thereof and intersects the first imaginary line behind the intersected mirror face and wherein the second path forms an angle with respect to the first path which is greater than said given angle; whereby two scans are effected from the mirror face for each oscillation of the mirror; and detecting the laser beam light directed at the moving target.

33. The method according to claim 32, wherein the means steps of directing comprises forming the first and second laser beams with a laser diode.

34. The method according to claim 32, wherein the steps of directing comprises forming the first and second laser beams with a single laser diode and splitting the laser beam from the laser diode.

35. The method according to claims 33 or 34, wherein the step for directing comprises reflecting the first and second laser beams with mirrors.

36. The method according to claim 32, wherein the steps of directing comprises forming the first and second paths with a non-zero acute angle of declination with respect to a plane perpendicular to the pivot axis.

37. The method according to claim 32, wherein the steps of directing comprise forming the first and second laser beams with a spot size having a given width in the scan direction and a given length in the direction of movement of the target and wherein the ratio of the length to the width is from 11-22 to 1.

38. The method according to claim 37, wherein the spot width is $\leq 0.011''$.

39. The method according to claim 32, wherein the moving target is a web moving in a transport direction.

40. The method according to claim 39, wherein the scan directions are perpendicular to the transport direction.

* * * * *